(12) United States Patent
Miller et al.

(10) Patent No.: US 7,592,154 B2
(45) Date of Patent: Sep. 22, 2009

(54) MODULATING SOS RESPONSE INDUCTION BY ANTIMICROBIAL AGENTS

(75) Inventors: Christine A. Miller, San Francisco, CA (US); Ronen Mosseri, Tel Aviv (IL); Stanley N. Cohen, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 61 days.

(21) Appl. No.: 11/498,208

(22) Filed: Aug. 1, 2006

(65) Prior Publication Data

US 2007/0031874 A1 Feb. 8, 2007

Related U.S. Application Data

(60) Provisional application No. 60/705,760, filed on Aug. 5, 2005.

(51) Int. Cl.
*C12Q 1/18* (2006.01)
*C12Q 1/02* (2006.01)

(52) U.S. Cl. .......................................... 435/32; 435/29
(58) Field of Classification Search ....................... None
See application file for complete search history.

(56) References Cited

U.S. PATENT DOCUMENTS 6,071,919 A * 6/2000 Theodore et al. ........ 514/252.12
2006/0286574 A1* 12/2006 Romesberg et al. ............ 435/6

OTHER PUBLICATIONS

Mattie, H. Antibiotic Efficacy in Vivo Predicted by in Vitro Activity; International Journal of Antimicrobial Agents, vol. 14 (2000) pp. 91-98.*
Wei et al. In Vivo Titration of Mitomycin C Action by Four *Escherichia coli* Genomic Regions on Multicopy Plasmids; Journal of Bacteriology, vol. 183, No. 7 (2001) pp. 2259-2264.*
Miller et al. SOS Response Induction by Beta-Lactams and Bacterial Defense Against Antibiotic Lethality; Science, vol. 305 (2004) pp. 1629-1631.*
Couterier et al. Bacterial Death by DNA Gyrase Poisoning; Trends in Microbiology, vol. 6, No. 7 (1998) pp. 269-275.*
Bacolla, A., et al., "PKD1 unusual DNA conformations are recognized by nucleotide excision repair," (2001) *The Journal of Biological Chemistry*, 276(May 25):18597-18604.
Biek, D., et al., "Involvement of integration host factor (IHF) in maintenance of plasmid pSC101 in *Eschericia coli*: mutations in the *topA* gene allow pSC101 replication in the absence of IHF," (1989) *Journal of Bacteriology*, 171(4):2066-2074.
Huisman, O., et al., "Cell-division control in *Eschericia coli*: specific induction of the SOS function SfiA protein is sufficient to block septation," (1984) *PNAS*, 81:4490-4494.
Ingmer, H., et al., "Destabilized inheritance of pSC101 and other *Escherichia coli* plasmids by DpiA, a novel two-component system regulator," (1998) *Molecular Microbiology*, 29(1):49-59.
Miller, C., et al., "DpiA binding to the replication origin of *Escherichia coli* plasmids and chromosomes destabilizes plasmid inheritance and induces the bacterial SOS response," (2003) *Journal of Bacteriology*, 185(20):6025-6031.

* cited by examiner

*Primary Examiner*—Jon P Weber
*Assistant Examiner*—Paul C. Martin
(74) *Attorney, Agent, or Firm*—Bozicevic, Field & Francis LLP; Pamela J. Sherwood

(57) ABSTRACT

Compositions and methods are provided for the use of SOS pathway targeted agents in antimicrobial formulations. The innate sensitivity of bacteria to antibiotics is increased by disrupting a mechanism that normally activates the bacterial SOS response or by inhibiting steps in the SOS response pathway itself. SOS response induction can result from exposure of bacteria to certain antibiotics, including β-lactam antibiotics and other agents that affect cell wall synthesis. By transiently delaying bacterial cell division, SOS response induction interferes with bacterial killing by ordinarily lethal concentrations of these drugs A pharmaceutical composition comprising an SOS targeted agent is administered to a patient suffering from a microbial infection, in combination with an antibiotic that induces an SOS response. The identification of the SOS pathway as a target for modulating antibiotic action provides a basis for further therapeutic development, through screening assays designed to detect molecules or genes that act on these pathways.

1 Claim, 4 Drawing Sheets

A

B

C

MODULATING SOS RESPONSE INDUCTION BY ANTIMICROBIAL AGENTS

CROSS-REFERENCE TO RELATED APPLICATIONS

This application claims the benefit of priority to provisional application 60/705,760, filed Aug. 5, 2005, which is incorporated herewith by reference.

This invention was made with Government support under contract 5R01 AI008619-37 awarded by the National Institutes of Health. The Government has certain rights in this invention.

BACKGROUND

The emergence of multi-drug-resistant pathogens has become a serious problem in the chemotherapy of bacterial infectious diseases. One of the strategies that can be used to overcome this problem is to find new bacterial protein targets that provide functions essential for cell growth or replication; and to screen for agents that disrupt in some way that essential function. Another strategy is to improve the efficacy of existing antimicrobial drugs by countering bacterial mechanisms of drug resistance.

As notorious as they may be, bacteria with inherited resistance to antibiotics are not the only reason that antibiotics fail, and may not even be the major reason. Contributing to resistance is the fact that growing populations of bacteria do not just die off when confronted with bactericidal antibiotics. Instead, their rates of mortality decline with time, and viable antibiotic-sensitive cells can be recovered even after hours of exposure to the drug. This phenomenon of declining sensitivity is well established for different species of bacteria and for different classes of antibiotics. Variously called "bacterial persistence", "phenotypic tolerance", or "adaptive resistance", the phenomenon remains a mystery with respect to its mechanism as well as its contribution treatment failure.

One mechanism postulated to account for the declining sensitivity and survival of bacteria confronted with bactericidal antibiotics is that growing populations of genetically identical bacteria continually generate subpopulations that are less sensitive to killing by antibiotics because they either are not growing or are dividing at very low rates.

The ability of bacteria to reduce their susceptibility to antimicrobial drugs importantly affects both bacterial ecology and the treatment of infectious diseases. Previously known mechanisms of bacterial defense against antibiotics include mutation of the drug target, inactivation or destruction of the antimicrobial, and inhibition of antibiotic entry. The present invention addresses the problem of innate susceptibility to antibiotics.

SUMMARY OF THE INVENTION

Bacterial defense mechanisms are manipulated in order to make the bacteria more susceptible to the effects of antibiotics. In one embodiment of the invention, methods are provided for increasing the innate sensitivity of bacteria to antibiotics by disrupting a mechanism that normally activates the bacterial SOS response. SOS response induction can result from exposure of bacteria to certain antibiotics, including β-lactam antibiotics and other agents that affect cell wall synthesis. By transiently delaying bacterial cell division, SOS response induction interferes with bacterial killing by ordinarily lethal concentrations of these drugs. Methods for disrupting the pathway that underlies this effect are demonstrated to accelerate cell killing by such antibiotics.

Methods and compositions are provided for the use of modulating agents targeted to the bacterial SOS response, including both the members of the canonical SOS induction pathway (in *E. coli* i.e. recA, lexA, sfiA) and members of the dpi operon. DpiA, the effector for the DpiBA two-component system, not only regulates transcription but also regulates DNA replication and segregation by virtue of its uncommon ability to bind to A+T-rich sequences in the replication origins of the *E. coli* chromosome and certain plasmids. Interaction of DpiA with replication origins competes with binding of the replication proteins DnaA and DnaB: When overexpressed, DpiA can interrupt DNA replication and induce the SOS response, thereby inhibiting cell division.

A pharmaceutical composition comprising an SOS targeted agent, for example an SOS inhibitory agent, is administered to a patient suffering from a microbial infection, particularly bacterial infections, in combination with an antibiotic that induces an SOS response, which may be formulated separately or together. The combined agents are effective at killing a variety of microbial organisms in vivo and in vitro.

DESCRIPTION OF THE SPECIFIC EMBODIMENTS

Figure 1:
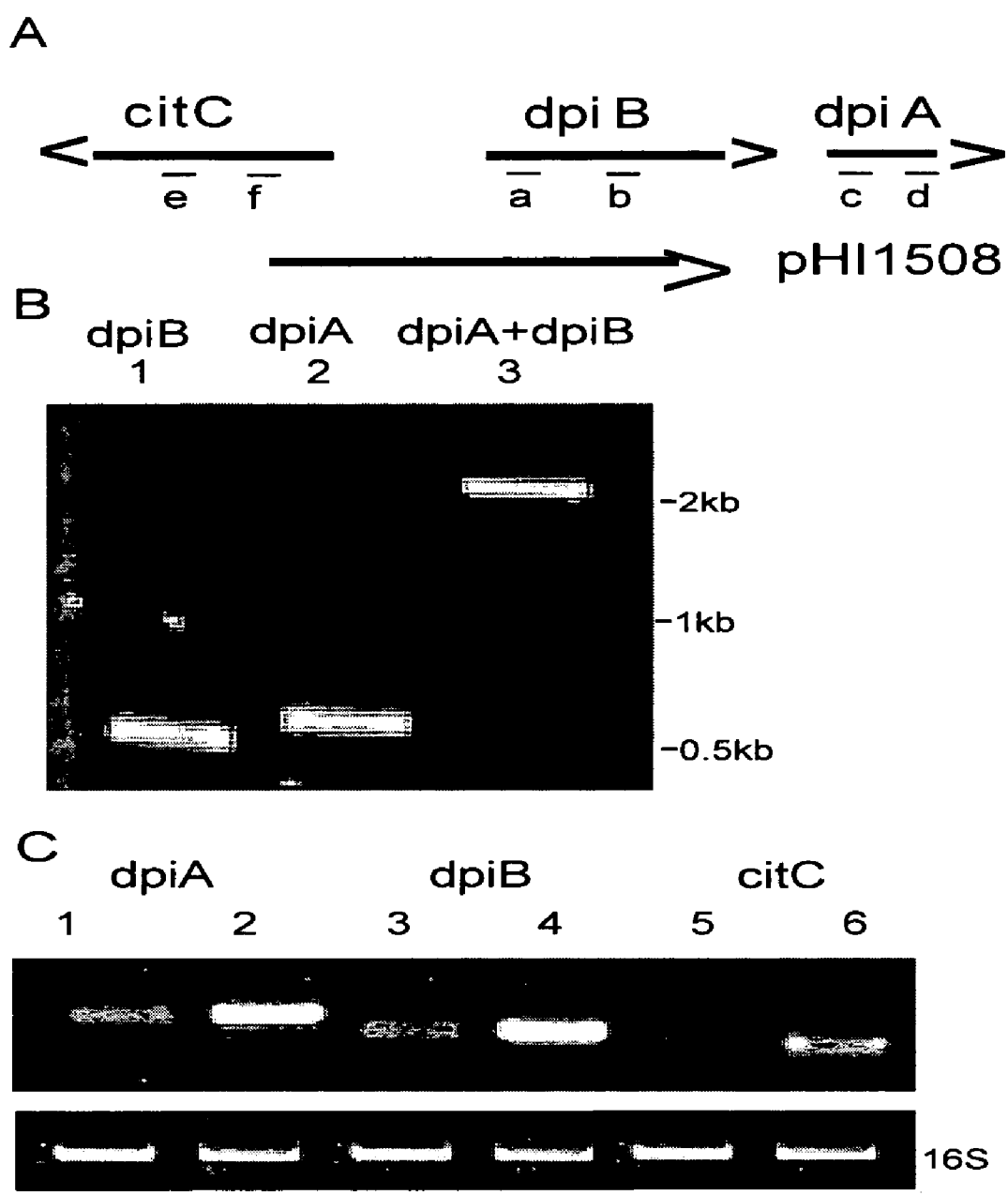
FIGS. 1A-1C. Structure and transcripts of the dpiBA operon. (A) The dpiB and dpiA genes are aligned in the 5'-3' direction; citC is 5' of the dpiBA promoter/operator region and is transcribed divergently from it. The segment of the dpiBA operon included in plasmid pHI1508 is indicated. (B) Agarose gel electrophoresis showing bands generated by reverse transcription PCR amplification of *E. coli* SC1088 RNA using pairs of oligonucleotide primers corresponding to sequences within dpiB (lane 1, primers a+b), dpiA (lane 2, primers c+d), or both genes (lane 3, primers a+d). Locations of primer sequences are indicated in (A). (C) Induction of dpi transcripts by ampicillin from SC1088 grown at 30° C. in the absence (lanes 1, 3, and 5) or presence (lanes 2, 4, and 6) of ampicillin (4 μg/ml for 4 hours), shown with loading controls. RNA extracted from SC1088 grown at 30° C. in the absence (lanes 1, 3 and 5) or presence (lanes 2, 4 and 6) of ampicillin (4 μg/ml for 4 hrs), was amplified quantitatively by RT-PCR (S2) using primers specific for dpiA (c+d; lanes 1 and 2), dpiB (a+b, lanes 3 and 4) or citC (e+f; lanes 5 and 6) and loaded onto agarose gels. Amounts of template RNA used and loaded onto gels were equal, as assessed by intensity of 16S rRNA bands (bottom panel).

Compositions and methods are provided for the use of antimicrobials or other agents that interfere with SOS induction. Methods are provided for increasing the innate sensitivity of bacteria to antibiotics by disrupting a mechanism that normally activates the bacterial SOS response. SOS response induction can result from exposure of bacteria to certain antibiotics, including antibiotics that affect cell wall synthesis, including β-lactam antibiotics. A pharmaceutical composition comprising an SOS targeted agent is administered to a patient suffering from a microbial infection, in combination with an antibiotic that induces an SOS response. The identification of the SOS pathway as a target for modulating antibiotic action provides a basis for further therapeutic development, through screening assays designed to detect molecules that act on this pathway.

DEFINITIONS

SOS pathway. In *E. coli* SOS response induction is an event that aids bacterial propagation by limiting cell division following insults that can affect the viability of progeny. Commonly, induction of the SOS pathway is a consequence of recA protein activation by its binding to single strand DNA regions that result from DNA damage or interrupted DNA replication. As shown by the experiments underlying this invention, the SOS pathway can also be induced by exposure of bacteria to other stresses, including certain antibiotics that affect cell wall synthesis, including β-lactam antibiotics. By transiently delaying bacterial cell division, SOS response induction prevents bacterial killing by ordinarily lethal concentrations of these drugs. In the case of the β-lactam antibiotics the induction of the SOS response relies on the DpiBA operon. In this operon, DpiA, the effector for the DpiBA two-component system, not only regulates transcription but also regulates DNA replication and segregation by virtue of its uncommon ability to bind to A+T-rich sequences in the replication origins of the *E. coli* chromosome and certain plasmids. Interaction of DpiA with replication origins competes with binding of the replication proteins DnaA and DnaB: when overexpressed, DpiA can interrupt DNA replication and induce the SOS response, thereby inhibiting cell division.

In one embodiment, the "SOS pathway", as used herein, is mediated by members of the dpiBA operon. In other embodiments, various genes that regulate and compose the SOS regulon (including recA, lexA or the downstream cell division inhibitor, sfiA) can mediate the SOS response in the absence of involvement by members of the dpiBA operon.

Such polypeptides include homologs and orthologs having at least about 20% sequence identity at the amino acid level, more usually at least about 40% sequence identity, and preferably at least about 70% sequence identity to the *E. coli* genes and regulon described herein.

Homology-based identification (for example, by a PILEUP sequence analysis) of enzymes can be routinely performed by those of skill in the art upon contemplation of this disclosure to identify those suitable for use in the methods of the present invention. Such polypeptides are usually produced in microorganisms, particularly bacteria.

The nucleic acid sequences encoding the above polypeptides may be accessed from public databases as cited herein. Identification of additional polypeptides is accomplished by conventional screening methods of DNA libraries or biological samples for DNA sequences having a high degree of similarity to known sequences.

The sequence of operon members may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet. 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated. The peptides may also be combined with other proteins to produce a fusion polypeptide.

Modifications of interest that do not alter primary sequence include chemical derivatization of polypeptides, e.g., acylation, acetylation, carboxylation, etc. Also embraced are sequences that have phosphorylated amino acid residues, e.g. phosphotyrosine, phosphoserine, or phosphothreonine.

The polypeptides may also be isolated and purified in accordance with conventional methods of recombinant synthesis. The reaction mixture may be purified using HPLC, exclusion chromatography, gel electrophoresis, affinity chromatography, or other purification technique.

The invention applies to the use of any antibiotic that is 1) more effective on rapidly growing cells (which is the general case for antibiotics since they target some process of cell growth) and which, 2) induces the SOS or stress response. Many antibiotics inhibit DNA replication or induce DNA breaks and these are known to induce SOS; others like the β-lactams had not been previously known to induce the SOS response, and others may not have been tested for their ability to affect the SOS response.

Beta-lactam antibiotic. (β-lactam) is a lactam with a heteroatomic ring structure, consisting of three carbon atoms and one nitrogen atom. The beta-lactam ring is part of several antibiotics, such as penicillin, which are therefore also called beta-lactam antibiotics. These antibiotics work by inhibiting the bacterial cell wall synthesis.

β-lactam antibiotics are indicated for the prophylaxis and treatment of bacterial infections caused by susceptible organisms. The development of broad-spectrum β-lactam antibiotics active against various Gram-negative organisms has increased the usefulness of the β-lactam antibiotics. All β-lactam antibiotics are bactericidal, and act by inhibiting the synthesis of the peptidoglycan layer of bacterial cell walls. The final transpeptidation step in the synthesis of the peptidoglycan is facilitated by transpeptidases known as penicillin binding proteins (PBPs). β-lactamantibiotics are analogues of D-alanyl-D-alanine—the terminal amino acid residues on the precursor NAM/NAG-peptide subunits of the nascent peptidoglycan layer. The structural similarity between β-lactam antibiotics and D-alanyl-D-alanine facilitates their binding to the active site of penicillin binding proteins (PBPs). The β-lactam nucleus of the molecule irreversibly acylates the Ser403 residue of the PBP active site. This irreversible inhibition of the PBPs prevents the final crosslinking (transpeptidation) of the nascent peptidoglycan layer, disrupting cell wall synthesis.

Common β-lactam antibiotics include narrow spectrum penicillins, e.g. benzathine penicillin; benzylpenicillin (penicillin G); phenoxymethylpenicillin (penicillin V); procaine penicillin; etc. Narrow spectrum penicillinase-resistant penicillins include methicillin; dicloxacillin; flucloxacillin. Moderate spectrum penicillins include amoxicillin and ampicillin. Extended spectrum penicillins include piperacillin; ticarcillin; azlocillin; and carbenicillin.

Cephalosporins include cephalexin; cephalothin; cephazolin; cefaclor; cefuroxime; cefamandole; cefotetan; cefoxitin; ceftriaxone; cefotaxime; ceftazidime; cefepime; cefpirome; etc.

Carbapenems include imipenem; meropenem; and ertapenem.

Unlike other beta-lactams, in monobactams there is no fused ring attached to beta-lactam nucleus. Thus, there is less probability of cross-sensitivity reactions. The only currently used member of this class is aztreonam.

Two areas of activity have been emphasized during the development of new beta-lactam antibiotics. The first area of emphasis is in developing compounds with extended gram negative spectrum. The second area of interest has been in the development of beta-lactamase resistant antibiotics. Due to emergence of beta-lactamase enzymes, the newer classes of beta lactam antibiotics are either resistant to or at least partially resistant to this form of enzyme degradation.

The term "effective amount" or "therapeutically effective amount" as used herein means a dosage sufficient to provide for treatment for the disease state being treated or to otherwise provide the desired effect. The precise dosage will vary according to factors such as subject-dependent variables (e.g., age, immune system health, etc.), the disease (e.g., the species of the infecting pathogen), and the treatment being effected. In the case of a pathogen infection, an "effective amount" is that amount necessary to substantially improve the likelihood of treating the infection, in particular that amount which improves the likelihood of successfully preventing infection or eliminating infection when it has occurred.

By "subject" or "individual" or "patient" or "host" is meant any subject for whom or which therapy is desired. Human subjects are of particular interest. Other subjects may include non-human primates, cattle, sheep, goats, dogs, cats, birds (e.g., chickens or other poultry), guinea pigs, rabbits, rats, mice, horses, and so on.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford, Ill.), Riedel de Haen A G (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L) isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included. SOS targeted antibiotic Compositions Compound Screening The present invention provides in vitro screening assays to identify agents that modulate activity of the SOS pathway. The screening assays are designed to identify agents that are useful as therapeutic agents in combination with antibiotics for treating bacterial infections. Both cell-based and cell-free assays are provided, as well as in silico rational design screening. Compounds may be screened by the computational modeling of the atomic interactions between drugs and members of the DpiBA operon or more generally of the SOS pathway.

Screening methods may also be used to screen for antibiotics, particularly β-lactam antibiotics that do not activate the SOS pathway, where such antibiotics provide for improved efficacy of treatment. In such methods, a candidate antibiotic is added to a cell, and the activation of the SOS pathway is determined, for example using a reporter assay as described in the Examples provided herein.

In some embodiments, the screening assays are cell-free screening assays. In these embodiments, the methods generally involve contacting an SOS pathway component with a test agent, and determining the binding, or biological effect, if any, on an activity of the polypeptide, e.g. the ability to bind DNA, induce an SOS response, etc. Pathway proteins may be obtained from a variety of known polypeptide and polynucleotide sequences among the bacterial species of interest.

In other embodiments, the methods provide cell-based assays. In these embodiments, the methods generally involve contacting a host cell with a candidate agent, and determining the effect, if any, on the induction of the pathway in the presence and absence of a candidate agent.

A variety of different candidate agents ("test agents") may be screened by the screening methods of the invention. Candidate agents encompass numerous chemical classes, though typically they are organic molecules, and may be small organic compounds having a molecular weight of more than 50 and less than about 2,500 daltons. Candidate agents comprise functional groups necessary for structural interaction with proteins, e.g., hydrogen bonding, and can include at least an amine, carbonyl, hydroxyl or carboxyl group, or at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In some embodiments, the candidate agents have a structure as set forth in Formula I.

Candidate agents, also referred to herein as "test agents") are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents that inhibit the activity of the SOS pathway induction or other components to the desired extent may be selected for further study, and assessed for cellular availability, cytotoxicity, biocompatibility, etc. For example, a candidate agent is assessed for any cytotoxic activity it may exhibit toward a eukaryotic cell, using well-known assays, such as trypan blue dye exclusion, an MTT ([3-(4,5-dimethylthiazol-2-yl)-2,5-diphenyl-2H-tetrazolium bromide]) assay, and the like. Agents that do not exhibit cytotoxic activity toward eukaryotic cells are considered candidate agents for use in therapeutic methods for treating a bacterial infection.

Cell-Free Assays

Cell-free assay methods generally comprise: a) contacting a test agent with a sample containing an SOS pathway polypeptide; and b) assaying an activity of the bacterial polypeptide in the presence of the substance, e.g. DNA binding, polypeptide binding, etc. An increase or a decrease in the measured activity in comparison to the activity in a suitable control (e.g., a sample comprising a polypeptide in the absence of the substance being tested) is an indication that the substance modulates an activity of the polypeptide.

An "agent that inhibits an activity of a bacterial SOS pathway polypeptide", as used herein, describes any molecule, e.g. synthetic or natural organic or inorganic compound, protein or pharmaceutical, with the capability of altering an activity of the polypeptide, as described herein. Generally a plurality of assay mixtures is run in parallel with different agent concentrations to obtain a differential response to the various concentrations. Typically one of these concentrations serves as a negative control, i.e. at zero concentration or below the level of detection. The activity can be measured using any assay known in the art.

A variety of other reagents may be included in the screening assay. These include reagents like salts, neutral proteins, e.g. albumin, detergents, etc that are used to facilitate optimal protein-ligand binding and/or reduce non-specific or background interactions. Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4° and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the amount of incorporated sulfate will then be detected.

Cell-Based Assays

Cell-based assay generally involve contacting a bacterial cell with a test agent, and determining the effect, if any, on an activity of the peptide. In some embodiments, cells comprising a mutated SOS pathway gene, as described herein, are used. Such mutations include but are not limited to those identified herein, as other genetic variants are readily obtained by screening, e.g. using the methods described herein, or may be synthetically produced. Such mutants are identified as those genetic changes in a bacterial SOS pathway sequence that provide for susceptibility to an SOS targeted antibiotic, e.g. a β-lactamase antibiotic. Mutants can also be generated by recombinant or other methods, e.g. targeting changes to the nucleotide binding site of the protein.

In these embodiments, a mutant bacterial cell comprising a susceptible SOS sequence is used. The mutant bacterium serves as a control, and is kept alive by providing necessary nutrients, and the like. A test bacterium comprises a functional copy of the SOS pathway. The test bacterium and the control bacterium are individually contacted (e.g., in separate cultures) with a test agent. A test agent that kills the test bacterium, as well as the control bacterium, is a candidate anti-bacterial agent. Viability of the bacterium is determined using standard methods, e.g., measuring the optical density of a culture grown in a liquid medium or plating the bacteria for viable cells on solid media.

It should be understood that in the drug screening and protein modification assays provided herein, a number of iterative cycles of any or all of the steps may be performed to optimize the selection. For example, assays and drug screens that monitor bacterial cell growth in the presence and/or absence of a potential inhibitor are also included in the present invention and can be employed as an assay or drug screen, usually as a single step in a multi-step protocol.

Once a potential modulator/inhibitor is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. The de novo synthesis of one or even a relatively small group of specific compounds is reasonable in the art of drug design.

The success of both database and de novo methods in identifying compounds with activities similar to the compound of interest depends on the identification of the functionally relevant portion of the compound of interest. For drugs, the functionally relevant portion may be referred to as a pharmacophore, i.e. an arrangement of structural features and functional groups important for biological activity. Not all identified compounds having the desired pharmacophore will act as a modulator of inflammation. The actual activity can be finally determined only by measuring the activity of the compound in relevant biological assays. However, the methods of the invention are extremely valuable because they can be used to greatly reduce the number of compounds that must be tested to identify an actual inhibitor.

In order to determine the biological activity of a candidate pharmacophore it is preferable to measure biological activity at several concentrations of candidate compound. The activity at a given concentration of candidate compound can be tested in a number of ways.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The SOS targeted antibiotics may be systemic after administration or may be localized by the use of an implant or other formulation that acts to retain the active dose at the site of implantation.

In one embodiment, the agents are co-formulated with an antibiotic that induces the SOS pathway response, e.g. a β-lactam antibiotic. In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing SOS targeted antibiotics is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others.

Preferred dosages for a given compound are readily determinable by those of skill in the art by a variety of means. A preferred means is to measure the physiological potency of a given compound.

Kits with unit doses of antibiotic, either in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods of Use

Formulations of SOS targeted agents and antibiotics are administered to a host suffering from or predisposed to a microbial infection. Administration may be topical, localized or systemic, depending on the specific microorganism. Generally the dose will be brought into contact with a microbial population. By contact is meant that the agent and the microorganism are brought within sufficient proximity of one another such that the agent is capable of exerting the desired effect on the microorganism. Contact may be achieved in any convenient manner, such as placing the agent in the same environment as the microorganism, and the like. An effective dose of the antibiotic will decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use.

Microbes of interest include, but are not limited to, Gram-negative bacteria, for example: *Citrobacter* sp.; *Enterobacter* sp.; *Escherichia* sp., e.g. *E. coli*; *Klebsiella* sp.; *Morganella* sp.; *Proteus* sp.; *Providencia* sp.; *Salmonella* sp., e.g. *S. typhi, S. typhimurium*; *Serratia* sp.; *Shigella* sp.; *Pseudomonas* sp., e.g. *P. aeruginosa*; *Yersinia* sp., e.g. *Y. pestis, Y. pseudotuberculosis, Y. enterocolitica*; *Franciscella* sp.; *Pasturella* sp.; *Vibrio* sp., e.g. *V. cholerae, V. parahemolyticus*; *Campylobacter* sp., e.g. *C. jejuni*; *Haemophilus* sp., e.g. *H. influenzae, H. ducreyi*; *Bordetella* sp., e.g. *B. pertussis, B. bronchiseptica, B. parapertussis*; *Brucella* sp., *Neisseria* sp., e.g. *N. gonorrhoeae, N. meningitidis*, etc. Other bacteria of interest include *Legionella* sp., e.g. *L. pneumophila*; *Listeria* sp., e.g. *L. monocytogenes*; *Mycoplasma* sp., e.g. *M. hominis, M. pneumoniae*; *Mycobacterium* sp., e.g. *M. tuberculosis, M. leprae*; *Treponema* sp., e.g. *T. pallidum*; *Borrelia* sp., e.g. *B. burgdorferi*; *Leptospirae* sp.; *Rickettsia* sp., e.g. *R. rickettsii, R. typhi*; *Chlamydia* sp., e.g. *C. trachomatis, C. pneumoniae, C. psittaci*; *Helicobacter* sp., e.g. *H. pylori*, etc.

Various methods for administration may be employed. The antibiotic formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific SOS targeted antibiotic to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously.

SOS targeted formulations are also useful for in vitro formulations to enhance killing of microbes. For example, SOS targeted formulations may be added to animal and/or human food preparations along with antibiotics. SOS targeted formulations may be included as an additive for in vitro cultures of cells, to prevent the overgrowth of microbes in tissue culture.

The susceptibility of a particular microbe to enhanced killing by antibiotics in conjugation with SOS targeted formulations may be determined by in vitro testing, as detailed in the experimental section. Typically a culture of the microbe is combined with SOS targeted formulations and antibiotics at varying concentrations for a period of time sufficient to allow the agent and antibiotic to act, usually between about one hour and one day. The viable microbes are then counted, and the level of killing determined.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXPERIMENTAL

Example 1

Two-component signal transduction systems have a key role in mediating the response of bacteria to environmental stimuli. Normally, receptor-mediated detection of a stimulus at the cell surface leads to autophosphorylation of a sensor kinase component, which then phosphorylates the effector protein component (i.e., the response regulator), enabling the effector to bind to operator/promoter sequences of target genes and either increase or repress transcription. DpiA, the effector for the DpiBA two-component system, not only regulates transcription but also regulates DNA replication and segregation by virtue of its uncommon ability to bind to A+T-rich sequences in the replication origins of the *E. coli* chromosome and certain plasmids. Interaction of DpiA with replication origins competes with binding of the replication proteins DnaA and DnaB: when overexpressed, DpiA can interrupt DNA replication and induce the SOS response, thereby inhibiting cell division.

Previous sequence analysis has suggested that the adjacent *E. coli* dpiB and dpiA genes, like their *Klebsiella pneumoniae* orthologs citA and citB, comprise a polycistronic operon (FIG. 1A). Polymerase chain reaction (PCR) analysis using combinations of primers corresponding to sequences within each of these genes confirmed that dpiB and dpiA are encoded by a common transcript (FIG. 1B). We wished to identify stimuli that activate the dpiBA operon; to monitor such activation, we fused a Hind III-Sma I DNA segment containing the region 5' to dpiB to a lacZ reporter gene fragment (pHI1508 in FIG. 1A) pHI1508 carries a HindIII-SmaI fragment containing the dpiBA operator/promoter and the first 1219 nucleotides of dpiB (indicated by the heavy bar), inserted into the StuI-HindIII sites of pHI1496, fusing it to the lacZ reporter gene (S1). β-Galactosidase synthesis from this construct was investigated under a variety of growth-limiting conditions known to activate two-component systems and/or the SOS response (including growth in media containing different carbon sources; starvation for $O_2$, $PO_4$, or carbon; heat or cold shock; high salt; exposure to ultraviolet light; culture in stationary phase or in conditioned media; and concentration to a high cell density).

Figure 2:
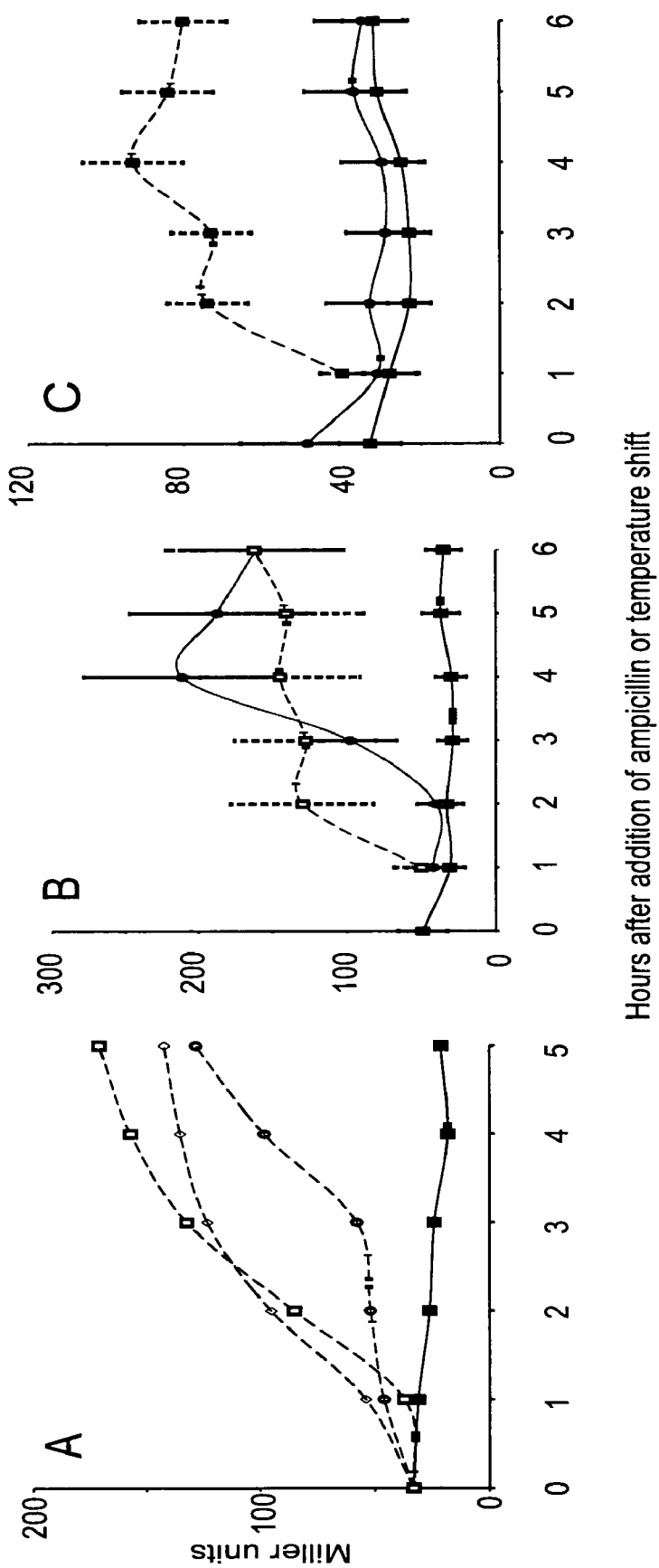
FIGS. 2A-2C. Induction of the dpi operon by β-lactam antibiotics. (A) Expression of the dpi operon as measured in lacZ⁻ *E. coli* strain UT481 by a lacZ reporter fusion to the dpiB promoter on pHI1508 [in Miller units]. Bacteria were grown at 30° C. with or without (black squares) antibiotics. Values similar to the control without antibiotics were observed after addition at time zero of kanamycin, streptomycin, spectinomycin, mitomycin C, chloramphenicol, tetracycline, nalidixic acid, rifampicin, vancomycin, or phosphomycin: Open symbols indicate lacZ expression after addition at time zero of ampicillin (squares), cephalexin (diamonds), or pipericillin (circles). Concentrations of antibiotics used: kanamycin (40 μg/ml), streptomycin (20 μg/ml), spectinomycin (40 μg/ml), mitomycinC (4 μg/ml), chloramphenicol (20 μg/ml), tetracycline (4 μg/ml), nalidixic acid (20 μg/ml), rifampicin (20 μg/ml) vancomycin (5 μg/ml), phosphomycin (2 μg/ml), ampicillin (4 μg/ml), cephalexin (40 μg/ml), or pipericillin (5 μg/ml). All antibiotics were added at approximately twice the MIC value for *E. coli*. All points represent the average of at least three separate experiments. (B) Induction of dpiB/lacZ (as measured by β-galactosidase expression calculated in Miller units) in *E. coli* JOE339, a lacZ⁻ mutant strain that carries an ftsI$^{ts}$ mutation. Cells were grown at 30° C. with (dashed line and open squares) or without (black squares) ampicillin (4 μg/ml), or at 42° C. in the absence of ampicillin (gray circles). (C) Same as (B) but in MC4100, the parent of JOE339. For (B) and (C), bars indicate SD.

Whereas none of the above conditions increased β-galactosidase synthesis, we observed during our experiments that expression of the reporter gene was stimulated by exposure of bacteria to ampicillin and other β-lactam antibiotics (penicillin, cefuroxan, cephalexin, pipericillin) (FIG. 2A). Induction of lacZ expression from the dpiB promoter fusion was dose dependent; sub-lethal amounts of ampicillin showed a lesser degree of expression. Neither lysis nor killing of bacteria by β-lactams was necessary for upregulation of the dpi operon. Bacteria that were more resistant to ampicillin than wild-type cells (e.g., fts mutants at permissive temperature) showed induction of the dpi operon after addition of β-lactams; however, induction of the dpi operon by ampicillin was not observed in ampicillin resistant bacteria carrying a plasmid borne gene encoding β-lactamase, which inactivates β-lactam antibiotics present in the culture media. In contrast, none of the non-β-lactam categories of antibiotics we tested activated the dpiBA promoter (FIG. 2A).

Increased expression of the dpiB and dpiA operon by β-lactam treatment was confirmed by quantitative PCR analysis (FIG. 1C), which showed a β-lactam-dependent fourfold increase in dpiBA transcripts encoded by the E. coli chromosome. Consistent with these observations was a concurrent threefold increase in expression of the E. coli citC gene (FIG. 1C), which is divergently transcribed from dpiBA (FIG. 1A) and previously was shown to be upregulated by overexpression of the DpiA protein. Similarly, lacZ fusions to promoters found in earlier studies to be activated by DpiA showed DpiA-dependent elevation of expression during treatment with ampicillin (Table 1), further establishing the ability of ampicillin to induce the dpiBA operon. Up-regulation of the dpiB/lacZ fusion by ampicillin was also observed in the dpiA null mutant strain (Table 1), indicating that induction of dpiBA expression by ampicillin does not require the DpiA protein.

A library of E. coli promoters fused to a lacZ gene fragment was constructed as follows: SC1088 chromosomal DNA was partially digested with Sau3AI and 1-2 kb fragments were gel extracted, purified, and ligated to the BamHI site of pHI1496, a lacZ expression vector conferring chloramphenicol resistance (S1). The strategy for selection of promoters activated by DpiA overexpression was to transform SC1088 pHI1449 competent cells (DpiA overproducer, ampicillin resistant) and select for blue colonies on LB media containing ampicillin, chloramphenicol, and X-gal (26 blue colonies out of 3200). Three clones were sequenced and found to contain a 5 kb insert in which the melR promoter region was fused to lacZ (pHI1626), a 300 bp fragment that includes the promoter region of pabA (pHI1627), and a 2.5 kb insert containing the 57-minute region of the E. coli chromosome (pHI1628).

TABLE 1

Induction of lacZ fusions by DpiA or ampicillin in wild-type (WT) and mutant strains. Ampicillin was added at 10 µg/ml and time points were taken after 2 hours of growth at 37° C. DpiA was overproduced at twice the normal amount from a multicopy plasmid pHI1429. pHI1627 carries a lacZ fusion to pabA, which has been identified as a gene up-regulated by DpiA. pHI1508 carries a lacZ fusion to the promoter/operator region of dpiB. The lacZ⁻ E. coli strain 1088 and null mutations of dpiA, recA and lexA were used. Values are averages of at least three experiments. β-Galactosidase production is indicated in Miller units.

| lacZ⁻ strain and plasmids | Miller units | Induction ratio |
|---|---|---|
| WT + pHI1627 | 29 ± 4 | |
| + DpiA overproduction | 118 ± 20 | 4 |
| + ampicillin | 185 ± 20 | 6.4 |
| dpiA null mutant + pHI1627 | 16 ± 5 | |
| + ampicillin | 18 ± 1 | 1 |
| WT + pHI1508 | 52 ± 3 | |
| + DpiA overproduction | 138 ± 25 | 2.8 |
| + ampicillin | 345 ± 50 | 6.6 |
| dpiA null mutant + pHI1508 | 27 ± 3 | |
| + ampicillin | 113 ± 15 | 4.1 |
| recA null mutant + pHI1508 | 24 ± 3 | |
| + ampicillin | 80 ± 8 | 3.3 |
| lexA null mutant + pHI1508 | 22 ± 6 | |
| + ampicillin | 110 ± 10 | 5 |

The lethality of β-lactam antibiotics stems from their interaction with transmembrane penicillin binding proteins (PBPs) and the consequent disruption of cell wall integrity. Whereas ampicillin binds to all 12 E. coli PBPs, pipericillin and cephalexin, which were among the β-lactam drugs we found to increase expression of the dpiBA operon, bind only to PBP3, which suggests that PBP3 specifically mediates the β-lactam effect. PBP3 is encoded by ftsI, one of a group of filamentation temperature-sensitive genes implicated in cell division, and is a membrane transpeptidase required for peptidoglycan synthesis at the septum generated by cell division. Binding of β-lactam antibiotics to PBP3 molecules at the septum inactivates transpeptidase function, leading to lysis of dividing cells in bacterial populations.

Inactivation of PBP3 also occurs when cultures of the ftsI$^{ts}$ strain, JOE339 ftsI23, are shifted to 42° C. We found that shift of JOE339 ftsI23 to 42° C. increased expression of the dpi/lacZ reporter gene fusion to a level similar to that observed after addition of ampicillin (4 µg/ml) to the culture medium (FIG. 2B). In contrast, expression from the dpi/lacZ fusion was unchanged at 42° C. in the parental strain (FIG. 2C); in a mutant of the rodA gene, which encodes PBP2 (a transpeptidase required for cell wall elongation) [strain S1]; or in a ts mutant of ftsZ [ftsZ84 in JOE337], a filamentation temperature-sensitive gene involved in septum ring formation. Collectively, these results strongly suggest that inactivation of PBP3 is a stimulus for increased expression of the dpiBA operon.

Figure 3:
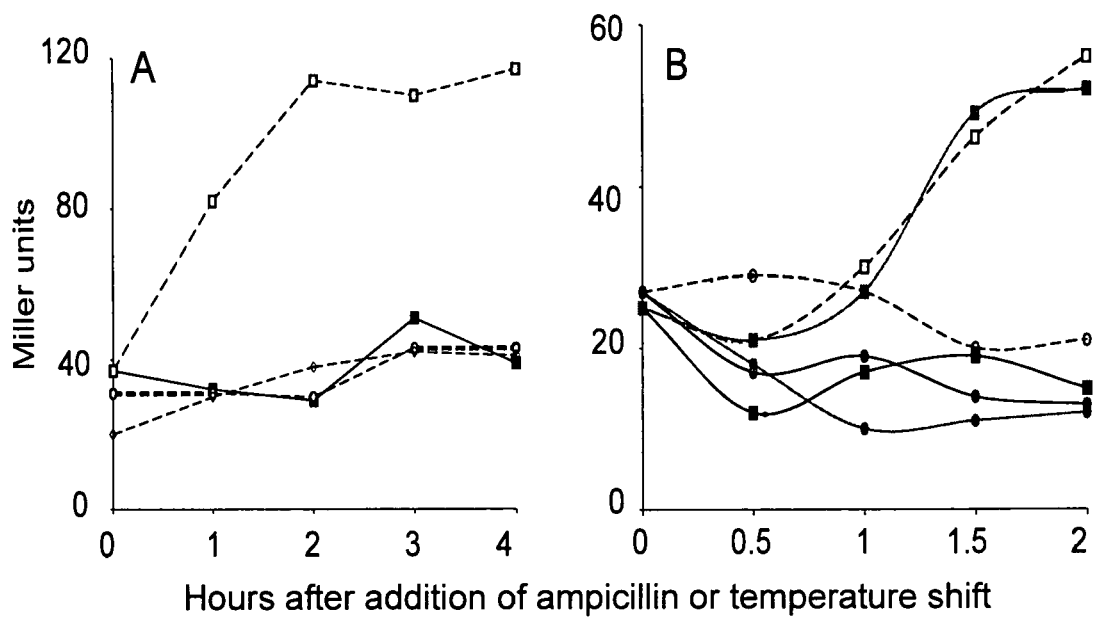
FIGS. 3A-3B. SOS response induced by PBP3 inactivation. (A) *E. coli* BR3151, a lacZ⁻ mutant strain containing a sfiA/lacZ fusion used to measure the SOS response, was grown in the absence (black squares) or presence (open squares) of ampicillin (4 μg/ml). Analogous experiments in the presence of ampicillin (4 μg/ml) used a dpiA (open circles) or recA derivative (open diamonds), which appear as overlapping lines. (B) Expression of the sfiA/lacZ fusion from ftsI$^{ts}$ JOE339 (squares) or dpiA JOE339 (diamonds) was followed by measuring β-galactosidase production (in Miller units) in bacteria grown at 30° C. in the absence (black solid lines, closed symbols) or in the presence (black dashed lines, open symbols) of ampicillin (4 μg/ml), or at 42° C. in the absence of ampicillin (gray lines, closed symbols). Both (A) and (B) are averages of three separate experiments. Strains were constructed by P1 transduction. Strain 1088 was transduced with phage P1 from *E. coli* strains containing recA::Tn10(S3) and lexA71::Tn5 (from Mary Berlyn, CGSC). Strain BR5171 is BR3151 (S4) containing a kanamycin resistance gene introduced into the dpiA locus to create a null mutation; another BR3151 derivative, BR7171, contains a Tn10 insertion in the recA locus to create a null mutation. In the absence of ampicillin, the values observed for all mutant strains were similar to that of the parent, BR3151. An sfiA/lacZ fusion closely linked to a kanamycin resistance marker (S5) was incorporated into the chromosome of ftsIts strain JOE339 and a JOE339 derivative containing a chloramphenicol resistance gene in the dpiA gene (S1).

A biological consequence of DpiA overexpression is induction of the SOS response; the extent of such induction can be determined by β-galactosidase synthesis from a lacZ fusion with the SOS-regulated promoter of the sfiA gene [e.g. Bacolla et al. (2001) J. Biol. Chem. 276, 18579; Hendricks et al. (2000) Mol. Microbiol. 36, 973], which prevents FtsZ polymerization and inhibits cell division when SOS is activated. Addition of ampicillin (4 µg/ml) to cell cultures increased lacZ expression from the fusion construct to a level comparable to that observed when DpiA was overproduced from a multicopy plasmid (FIG. 3A). However, we observed no change in sfiA/lacZ expression in bacteria containing a dpiA null mutation (FIG. 3A); this result implies that the increase in sfiA expression by ampicillin requires dpiA function. β-Galactosidase synthesis by the sfiA/lacZ fusion construct was also increased by shifting of the ftsI$^{ts}$ strain to 42° C., further establishing the ability of FtsI/PBP3 inactivation to induce SOS (FIG. 3B). This result, which identifies SOS as a response to impaired cell septum synthesis, was also dependent on an intact dpiA gene (FIG. 3B).

Mutations in recA or lexA that preclude induction of the SOS response prevented the effects of either ampicillin treatment or temperature shift of the ftsI mutant strain on expression of the sfiA/lacZ fusion protein (FIG. 3A), confirming that sfiA induction by the β-lactam-PBP3-DpiA pathway is SOS dependent. Still further confirmation that the observed activation of sfiA expression by this pathway is due to induction of the SOS response was provided by Western blot data showing that the RecA protein also was elevated by DpiA overproduction and by inactivation of PBP3 through ftsI temperature inactivation or by ampicillin, and that the effect of PBP3 inactivation was dependent on an intact dpiA gene. The dependence of β-lactam/PBP3-mediated SOS induction on dpiA contrasted with the lack of effect of the dpiA mutation on RecA expression induced by the DNA damaging agent mitomycin C, indicating the distinctive nature of the cell wall-mediated and DNA damage-mediated paths to SOS induction.

Western blot analysis using anti-RecA antibody showed 1.7±0.3 fold RecA protein increase in wt stain 1088 when the DpiAexpressing plasmid pHI1447 was present; addition of 4 µg/ml ampicillin resulted in a 1.9±0.4 fold increase and of mitomycinC (4 µg/ml), a 1.5±0.2 fold increase. In the ftsIts strain JOE339 there was a 1.7±0.4 fold increase in the amount of RecA protein after one hour incubation at 42° C. In the dpiA::Km null, mutant no increase in RecA protein was observed upon addition of ampicillin; in contrast mitomycinC addition resulted in a 2.0±0.3 fold increase in the amount of RecA protein. The numbers are normalized to loading controls and an internal standard and are relative to the value observed in the absence of induction. The results above are an average of three experiments after one hour of exposure to the indicated condition. Chemiluminescence of bands was quantitated using a BioRad Versadoc 1000 instrument.

Because β-lactam antibiotics kill only bacteria that are dividing, we hypothesized that the ability of these drugs to induce the SOS response, and consequently delay cell division by increasing the expression of sfiA, may provide temporary protection from β-lactam lethality. We therefore tested wild-type E. coli cells, dpiA null mutant bacteria, bacteria known to be unable to generate an SOS response [i.e., recA mutant cells], and sfiA mutant bacteria for their relative ability to withstand exposure to ampicillin, as measured by survival in cultures containing different concentrations of this antibiotic.

Mutation of dpiA, recA, or sfiA increased bacterial susceptibility to killing by ampicillin (FIG. 4): 90% of cells mutated in these genes were unable to form colonies after 1 hour of exposure to ampicillin (3 µg/ml), whereas the same extent of killing of wild-type cells required 1 hour of exposure to ampicillin at 9 µg/ml or 4 hours of exposure at 3 µg/ml. During overnight exposure to pipericillin (2 µg/ml), a PBP3-specific β-lactam, 10 times as many wild-type bacteria as dpiA mutant bacteria survived (0.01% versus 0.001% of cells relative to the number before addition of antibiotic). However, the minimum inhibitory concentration of ampicillin required to permanently inhibit cell growth (1.5 µg/ml) was unchanged by mutation of dpiB, dpiA, or both. Thus, although dpiBA-mediated induction of the SOS response delayed α-lactam antibiotic lethality, it did not reverse the effects of extended exposure to these drugs.

Figure 4:
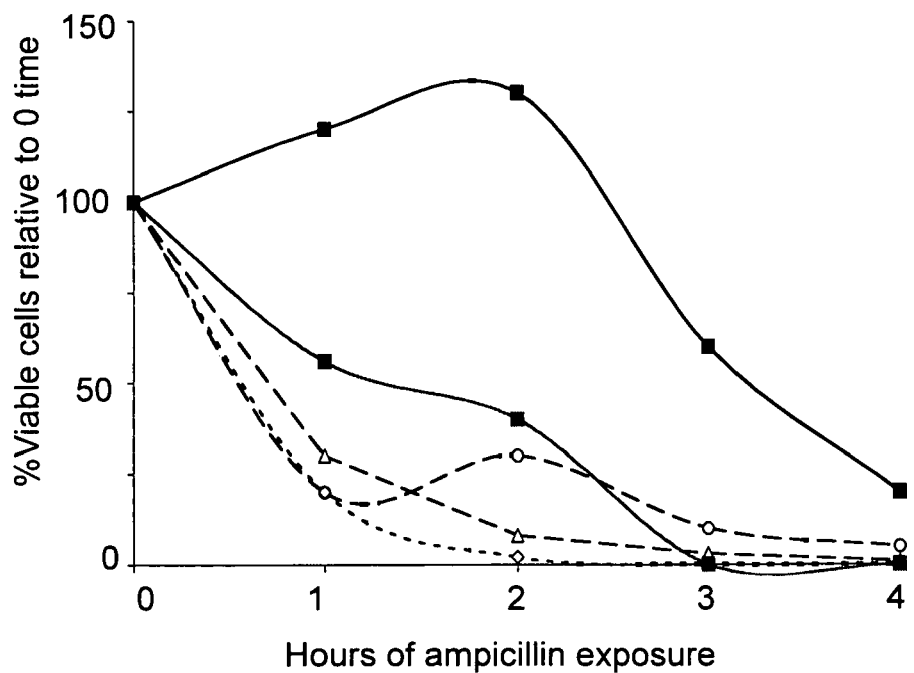
FIG. 4. Effect of SOS response induction on survival of bacterial cells expressing DpiA during β-lactam exposure. SC1088 wild-type (squares) cultures were exposed to ampicillin at time zero, and percent survival was determined. Survival data are also shown for strains containing null mutations in recA (open diamonds), dpiA (open circles), or sfiA (open triangles). Ampicillin was added at 3 μg/ml (black lines) or 9 μg/ml (gray lines). Percent survival was determined by counting of colony forming units (cfu's), at least 200 colonies were counted per time point, and plotted as a function of exposure time before exposure or after exposure to antibiotics.
Figure 5:
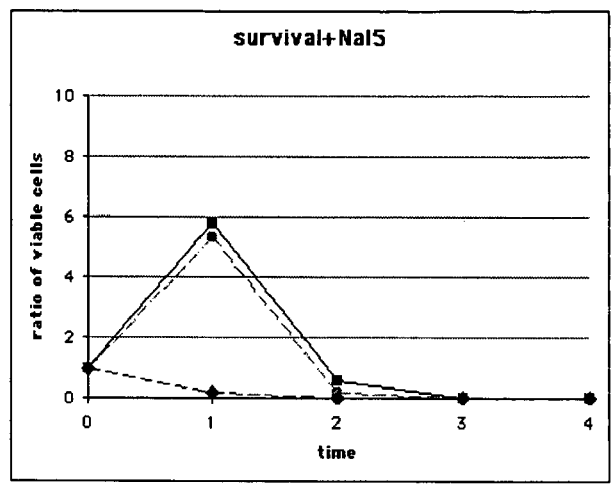
FIGS. 5A-5C. Effect of antibiotics on bacterial cells with an intact or defective SOS response.
Figure 5:
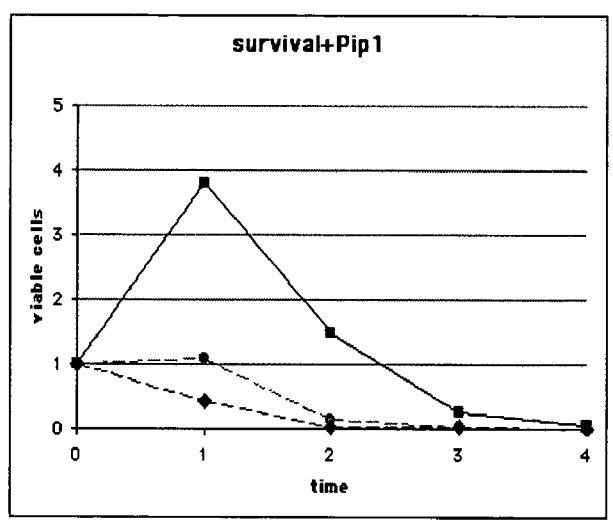
Figure 5:
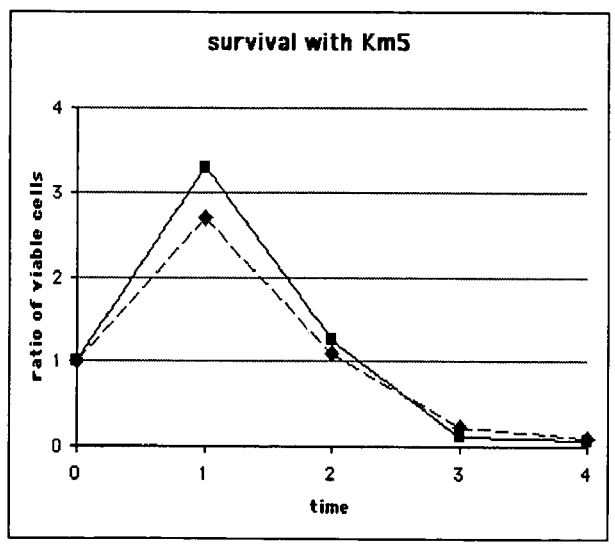

The experiments shown in FIG. 4 were repeated with the antibiotics: naladixic acid, at 5 µg/ml; pipericillin, at 1 µg/ml; and kanamycin at 5 µg/ml. As shown in FIGS. 5A-5C, the black squares are wild type cells, strain SC1088, the green circles are the dpiA null strain in that background, and the red diamonds are the recA mutation in that background. The data demonstrate that antibiotics that induce the SOS response, such as naladixic acid; as well as antibiotics of the β-lactam family, which are shown herein to induce the SOS response, are more effective, i.e. there is less survival, if the SOS response cannot be induced, as shown in the recA mutant cells. Antibiotics that do not induce the SOS response, such as kanamycin, are equally effective against the wild type or mutant bacteria.

Our results indicate a hitherto unsuspected role for the SOS response in temporarily halting cell division when the transpeptidase encoded by the ftsI gene at the cell septum is functionally impaired, and additionally demonstrate a novel role for both the DpiBA two-component system and the sfiA gene in this process. The consequence of dpiBA operon-dependent induction of SOS by β-lactam antibiotics is to mitigate the lethal effects of these drugs on bacteria. Recent evidence indicates that even subinhibitory concentrations of a variety of antibiotics can modulate transcription in bacteria, and microarray data suggest that altered expression of SOS and other stress response genes are among the many global changes that can result from exposure to antibiotics. Additionally, induction of the SOS response also can affect the interbacterial transfer of genetic material, increasing dissemination of antibiotic resistance among microbial populations. The further ability of the SOS response to enhance the survival of bacteria exposed to β-lactams identifies the SOS response as a potential target for drugs aimed at enhancing the efficacy of β-lactam antimicrobials.

What is claimed is:

1. A method of screening for an antibiotic enhancing agent, the method comprising:
   a) contacting a cell containing an SOS pathway polypeptide comprising dpiA, dpiB, recA, lexA or sfiA, with a candidate agent;
   b) determining the effect of said agent on SOS pathway polypeptide function; and
   c) determining the effect of said agent on said antibiotic function by
      i) assaying the lethality of said antibiotic on said cell in the presence of said agent and in the absence of said agent, and
      ii) comparing the said effects,
   wherein increased lethality in the presence of said agent than in the absence of said agent indicates that the agent enhances antibiotic function; and wherein an antibiotic enhancing agent is one that disrupts said SOS pathway polypeptide function and enhances said antibiotic lethality.

* * * * *